United States Patent [19]

Shimada et al.

[11] 4,247,819
[45] Jan. 27, 1981

[54] APPARATUS FOR SURFACE FLAW DETECTION ON ELECTRICALLY CONDUCTIVE CYLINDRICAL MATERIAL

[75] Inventors: Katsuhiko Shimada, Yokohama; Isamu Komine, Yokosuka; Hideya Tanabe, Yokohama, all of Japan

[73] Assignee: Nippon Kokan Kabushiki Kaisha, Tokyo, Japan

[21] Appl. No.: 943,865

[22] Filed: Sep. 19, 1978

[30] Foreign Application Priority Data

Sep. 22, 1977 [JP] Japan .................................. 52/113200
Sep. 22, 1977 [JP] Japan .................................. 52/113201
Sep. 22, 1977 [JP] Japan .................................. 52/113202

[51] Int. Cl.³ ........................ G01N 27/82; G01R 33/12
[52] U.S. Cl. .................................. 324/233; 324/237; 324/262
[58] Field of Search ........ 324/225, 226, 228, 234–243, 324/262, 233

[56] References Cited

U.S. PATENT DOCUMENTS

| | | | |
|---|---|---|---|
| 2,353,211 | 7/1944 | Zuschlag | 324/238 |
| 3,244,972 | 4/1966 | Fisher | 324/226 |
| 3,271,662 | 9/1966 | Quittner | 324/233 |

Primary Examiner—Gerard R. Strecker
Assistant Examiner—Walter E. Snow
Attorney, Agent, or Firm—Haseltine and Lake

[57] ABSTRACT

A surface defect detecting apparatus having at least one sensor block for movement in respect of rotating cylindrically shaped electrically conductive metallic material to be inspected by scanning an outer portion of the surface of the material. The sensor block has spaced guide wheels at front and rear parts thereof in the spiral scanning direction which rotate in response to the rotation of the material; and a coil holder for supporting a plurality of eddy-current flaw detecting coils arranged longitudinally in a row in the direction of movement, intermediate between pairs of guide wheels at the front and rear parts opposite to the outer surface of said material with a predetermined gap therebetween. A turning wheel at each of the front and rear parts of the coil holder is rotatable with respect to the outer surface of the material so as to maintain the predetermined gap.

An AC signal of a predetermined frequency applied from an oscillator to the coils produces corresponding eddy currents in material to be inspected. The coils are divided into a first group and a second group with one group of coils being defined by coils other than those coils in an adjoining row to that group, phase shifters feed the AC signal to coils of the first group resulting in a shift in phase by a predetermined amount, as reference signal to detectors formed as phase detectors. The phase detectors are associated with coils of the latter group, with a phase different from that of the AC reference signal respectively applied to a second group of coils and to the phase detectors of the first group of coils.

5 Claims, 11 Drawing Figures

APPARATUS FOR SURFACE FLAW DETECTION ON ELECTRICALLY CONDUCTIVE CYLINDRICAL MATERIAL

BACKGROUND OF THE INVENTION

The present invention relates to a surface defect detecting apparatus for use with electrically conductive materials having a circular external shape, such as steel round billets, round bars, carbon electrodes, steel pipes, etc.

Among the automatic flaw detecting apparatus heretofore known in the art for detecting the surface defects of round billets are those which are called as magnetic flaw detecting apparatus. Although this flaw detecting apparatus has the advantage of automatic flaw detection over the known magnetic particle flaw detection method, there is a disadvantage that since magnetic flux is passed from an electromagnet through a rotating round billet and the resulting leakage flux from a defective area is detected by sensors such as magnetism responsive diodes, the sensors must be arranged in close proximity to the surface of a round billet with a very small gap of the order of 0.2 mm, with the result that the presence of an oval or projection makes it impossible to effect the detection and consequently the outer surface of the billet must be preliminarily prepared. Another disadvantage is that since each sensor is provided with a shoe which contacts with the round billet surface to maintain the very small gap, the oxide particles on the round billet surface tend to deposit in the very small gap at the shoe or the gap between the diode surface and the round billet surface, thus producing ill effects on the detecting capacity. Still another disadvantege is that since the sensors are semiconductor devices, the sensors are easily affected by heat and it is impossible to detect flaws in a heated round billet without cooling means. Of course, the generation of heat due to the friction of the shoes makes it impossible to effect the desired high speed scanning. Still another disadvantage of the leakage flux detection method is that if the depth of flaws is greater than 2 mm, for example, the amplitude of the outputs becomes constant thus making it impossible to discriminate the magnitude of the flaws, and moreover if a part of the coil departs from the end of the round billet, the detection characteristic is changed and consequently a portion of the round billet end corresponding to the diameter of the magnetic flux coil fails to be subjected to the flaw detection, the portion usually amounting as much as 40 mm.

In the course of the investigations to overcome the foregoing deficiencies, a surface defect detecting apparatus for detecting by a so-called eddy-current flaw detecting method surface defects of a material having a circular external shape has been proposed. In this proposed surface defect detecting apparatus, the input-output characteristic of an eddy-current flaw detecting coil is linearized by using it in combination with a feedback amplifier and a surface defect is detected in the form of a change in the impedance of the coil, thus ensuring a relatively large gap between the sensor and the surface of a material to be inspected for defects and thereby making it possible to effect a continuous flaw detection. A plurality of such flaw detecting coils are arranged in a row and the length of the row is selected as a scanning width, thus making it possible to effect the desired flaw detection efficiently at a wide scanning width. However, where a plurality of such coils are arranged in a row to effect the eddy-current flaw detection with a wide scanning width, there is the disadvantage of causing an error in the result of flaw detection due to mutual interference caused by the inductive coupling between the adjoining flaw detecting coils. If, for example, the coils are arranged at intervals to eliminate such error, there is a disadvantage that the spacing between the coils results in a portion not subjected to the flaw detection. While, in order to overcome this difficulty, it may be conceived to arrange the coils in the spacing at a distance of a predetermined dimension so that the coils are as a whole arranged in a planar staggered lattice pattern, this arrangement is also disadvantageous in that the construction of the coil assembly becomes complicate when applied to the flaw detection of round or cylindrical materials, that adjustment is essential to ensure conformity with the curvature of the external sectional form of a material to be inspected so as to ensure a fixed gap between the surface of the material and the coils and so on. Another technique of shifting a distance corresponding to the coil spacing and thereby eliminating the occurrence of uninspected portions as a matter of sequence also has the disadvantage of increasing the flaw detecting time by two times and deteriorating the detecting efficiency.

On the other hand, while an attempt may be conceived to provide an electromagnetic shielding by enclosing the coils with a nonmagnetic metal, this also has the disadvantages of making the construction of the coil assembly itself more complicate, difficulty to provide a complete shilding and the resulting improvement in flaw detection accuracy falling short of what is expected.

The above-mentioned proposed surface defect detecting apparatus is designed so that in order to spirally scan closely the outer surface of a material, e.g., round billet turned on its axis at a predetermined speed, each sensor or a row of eddy-current flaw detecting coils is mounted on a sensor block adapted for movement at a controlled speed in the lengthwise direction of the round billet in contact with the outer surface of the round billet through its front and rear guide rollers and the sensor block causes the coil assembly to follow the bending of the round billet. However, there is a disadvantage that if the forward end of the sensor block departs from the round billet, the parallel gap between the lower surface of the sensor and the billet surface will be slanted thus causing an error in the result of flaw detection and thereby giving rise to the similar problem to the previously mentioned problem of uninspected end portion. As a solution to this problem, with a view to maintaining the gap size between the sensor and the outer surface of a material to be inspected constant at the end portion of the material, as for example, a supporting member may be mounted on a fixed member so that when the leading rollers of the guide roller pairs respectively provided at the front and rear parts of the sensor in spaced relation run off the end of the material, the supporting member upwardly supports the forward end of the sensor block and in this way the sensor is maintained in the desired position by means of the supporting member and the trailing rollers. However, as frequently experienced with round billets or steel pipes, in the case of a defective rolled product, particularly in the case of a material having an end bending, the presence of bending in the portion nearer to the end than the trailing rollers causes the bent portion to rotate eccentrically so that the material is moved toward and away from the sensor in response to its rotation and consequently not only the gap size between the sensor lower surface and the material surface is periodically varied producing an ill effect on the measurement result, but also there is the danger of the sensor being damaged by the end of the material depending on the degree of the bending. In addition to such end bending, such defects as nonuniform bending and swell will inevitably be caused in the ordinary round billets or steel pipes during their manufacture, with the result that there are many instances where the rotational conditions must be changed for each of materials to be inspected and consequently it is extremely difficult to adjust the position of the supporting material to obtain the desired detection accuracy in relation to the pattern of changes in the gap size, the peripheral speed, etc. Where the material to be inspected is a rolled round billet, if there is any fin-like oval projection in the vicinity of its end, there is the danger of the sensor being damaged by the oval.

SUMMARY OF THE INVENTION

It is a principal object of the invention to provide a surface defect detecting apparatus comprising a plurality of flaw detectors each consisting of a flaw detecting coil, an amplifier for converting a part of the coil into a positive feedback impedance and a phase detector, the detectors being arranged in a manner that a sensor is provided comprising the flaw detecting coils arranged in a row in the axial direction of a material to be inspected, whereby the outer surface of the material is subjected to a spiral flaw detection at a wide scanning width with a high degree of efficiency and moreover the occurrence of ill effects on the result of flaw detection due to mutual interference by the inductive coupling between the adjoining coils is electrically eliminated thus ensuring improved flaw detecting accuracy.

It is another object of the invention to provide a surface defect detecting apparatus capable of stably performing, while ensuring a high flaw detecting accuracy, the desired flaw detecting operation at a high scanning speed up to the extreme limit of the end of a material to be inspected.

It is still another object of the invention to provide a surface defect detecting apparatus which is capable of ensuring an effective follow-up to the bending in a material to be inspected, always maintaining constant the gap between the lower surface of sensors and the surface of the material, eliminating the danger of the sensors being damaged by any irregularity in the surface of the material, minimizing the uninspected end portion and simplifying the adjusting operation required by a change in the size or outer diameter of materials to be inspected.

In accordance with the present invention, there is thus provided an eddy-current surface defect detecting apparatus in which each flaw detection signal system comprises an eddy-current flaw detecting coil disposed opposite to a meterial to be inspected, an amplifier constituting a feedback loop which provides compensation for the nonlinearity between the magnitude of a defect and a change in the impedance and a phase detector for subjecting to phase detection the amplifier output corresponding to the impedance change, and a plurality of the systems are provided in a manner that an integral sensor is provided in which the coils are arranged in a row. Each of the coils consists of two coil elements one of which is connected between the output terminal and the noninverting input terminal of the amplifier to form a positive feedback impedance and the other coil element is connected between the ground terminal of the flaw detection signal system and the amplifier noninverting input terminal. A sinusoidal AC signal is applied to the other input terminal or inverting input terminal of the amplifier, and the AC signal is applied serially to the two coil elements from the output terminal of the amplifier so that the AC signal is subjected to voltage division and the resulting voltage is applied as a positive feedback signal to the amplifier non-inverting input terminal from the junction point of the coil elements. The coil elements are both arranged opposite to the surface of the material with a predetermined gap therebetween. Thus, with the material being moved relative to the coil elements, when a defective area in the surface of the material passes just below the coil elements, there occurs a change in the impedance which is proportional to the depth of the surface defect. There are provided an oscillator circuit for generating said AC signal of a predetermined frequency and a first phase shifter connected to the oscillator so as to apply to the adjoining flaw detecting coils the AC signal in different phase relation with respect to each other, and further provided are two second phase shifters each adapted to apply, in common to the respective group, a desired flaw detecting phase to the phase detectors for one of two signal system groups one of which includes the respective signal systems including the alternate ones of the plurality of flaw detecting coils and the other group includes the respective signal systems including the other alternate ones of the flaw detecting coils which are adjacent to the first alternate coils. The coils in one of the two signal system groups are adapted to receive for example the AC signal applied directly from the oscillator and also the oscillator output is applied as a synchronizing signal to the phase detectors in the system group through one of the second phase shifters. On the other hand, the oscillator output which has been shifted in phase through the first phase shifter is applied to the coils in the other system group and the output of the first phase shifter is applied as a synchronizing signal to the phase detectors in the same group through the other second phase shifter. The phase difference provided by the first phase shifter may be determined as desired and in fact it should preferably be 90 degrees. Thus, if the selected phase difference is 180 degrees, it is only necessary to provide as the first phase shifter a phase inverting circuit to follow the sinusoidal signal generating oscillator. In this way, each of the coils in the row is energized by the AC signal which is different in phase from the AC signal applied to the adjoining coil, and consequently if the alternate coils are for example formed into one signal system group so that the coils belonging to the one signal system group are arranged alternate with the coils belonging to the other signal system group, as regards the coil spaces one extra pitch will in effect be obtained so far as the inductive coupling is concerned. Of course, if three different phases are used and the coils are formed into three signal system groups, with the same arrangement, as regards the coil spaces two additional pitches will be obtained so far as the inductive coupling is concerned. When a surface defect causes a change in the impedance of the coil of each signal system, the resulting output signal is subjected to phase detection by the synchronizing signal of the phase corresponding to the group to which said signal system belongs, with the result that the coil is not affected by the signals from the signal systems associated with the adjoining flaw detecting coils and each coil constitutes a separate system in either of the groups. In this way, the accuracy of flaw detection by the plurality of the coils arranged in a row can be made in effect as high as that of a single coil, and deterioration of the detecting accuracy due to interference between the adjoining coils can be prevented.

The sensor comprising the plurality of flaw detecting coils arranged in a row is supported on a sensor block in a manner that the row is directed in the axial direction of a material to be inspected having a circular external sectional form and turned on its lengthwise direction axis, and the sensor block sits astraddle on the material to scan its outer surface. The sensor block is composed of a supporting base member suspended from a carriage movably hanged on supporting girders which are installed just above a turning roller unit adapted to rotate the material, a slide base plate mounted to the supporting base member to be slidable in a direction at right angles to the lengthwise direction of the material, a pair of follow-up wheel unit each comprising two guide wheels which are spaced away from each other in the direction of the said sliding motion and rotated by the rotation of the material in contact with the outer surface thereof, a follow-up base plate supporting the pair of the follow-up wheel unit in a spaced relation in the lengthwise direction of the material, the follow-up base plate being coupled to the slide base plate through first resilient means in a direction to press the follow-up wheel unit against the material, a sensor holder supporting the sensor and coupled through second resilient means to the follow-up base plate within the space between the guide units so as to rotatable about its axis which is directed in the said sliding direction, and a pair of turning wheels mounted at the lengthwise direction ends of the sensor holder within the space between the follow-up wheel units so as to be rotated by the rotation of the material in contact with its outer surface and thereby to maintain at a predetermined value the gap size between the lower surface of the sensor mounted to the central portion of the sensor holder and the surface of the material. The carriage includes pressure means for pressing guide wheels and the turning wheels against the surface of the material through the slide base plate, the follow-up base plate and the first and second resilient means by pressing the supporting base member.

The sensor is also provided at least on one side of the sensor holder central portion with another guide wheel adapted for rotation in contact with the surface of the material, and the sensor of further includes a sensor lower surface protective member provided at least at one end of the sensor holder and between the sensor and the turning wheel, the protective member projecting beyond the sensor lower surface and having a bottom surface positioned above the lower end of the turning wheel.

Thus, the apparatus of this invention has among its great advantages the fact that the desired flaw detection can be effected all over the surface of a round billet having ovals without damaging the flaw detecting coils, that the use of the eddy-current flaw detection method has the effect of reducing the size of the coils and ensuring a flaw detecting characteristic having a wide linearity even at a distance of for example 5 mm from the billet surface to the coils, that the sensor uses no simiconductor devices but comprises only the coils thereby making it possible to effect the desired flaw detection even in the case of round billets of for example over 80° C., and that the depth of defects can be discriminated in a plurality of ranges thus allowing automation of the corresponding markings.

Another advantage of this invention is that the flaw detecting means disposed to oppose a material to be inspected is in no way complicated in construction and moreover the flaw detection can be effected with a high degree of accuracy due to the fact that the material can be scanned closely at a wide scanning width corresponding to the width of the coil assembly and that the no ill effect is produced on the result of flaw detection by mutual interference between the coils during the flaw detection.

Still another advantage is that the sensor is guided to follow the bending of a material to be inspected having a circular sectional external form and thereby to always maintain at a predetermined value the gap size between the sensor lower surface and the surface of the material even in the face of any irregular projections or recesses in the material surface, that there is no danger of the sensor being damaged at the end of the material and the noninspected end portion can also be reduced, and that the apparatus can be adapted to conform with materials having a variety of external shapes, thus eliminating the need to readjust the spacing between the guide wheels and thereby eliminating any extra operation in case of a change in the size of materials to be inspected.

The above and other objects, features and advantage of the present invention will appear more apparent from the following description taken in conjunction with the accompanying drawings.

DESCRIPTION OF THE PREFERRED EMBODIMENTS

The present invention will now be described in greater detail with refference to the illustrated embodiments in which the invention is applied to an eddy-current flaw detecting apparatus for use with round billets.

Figure 1:
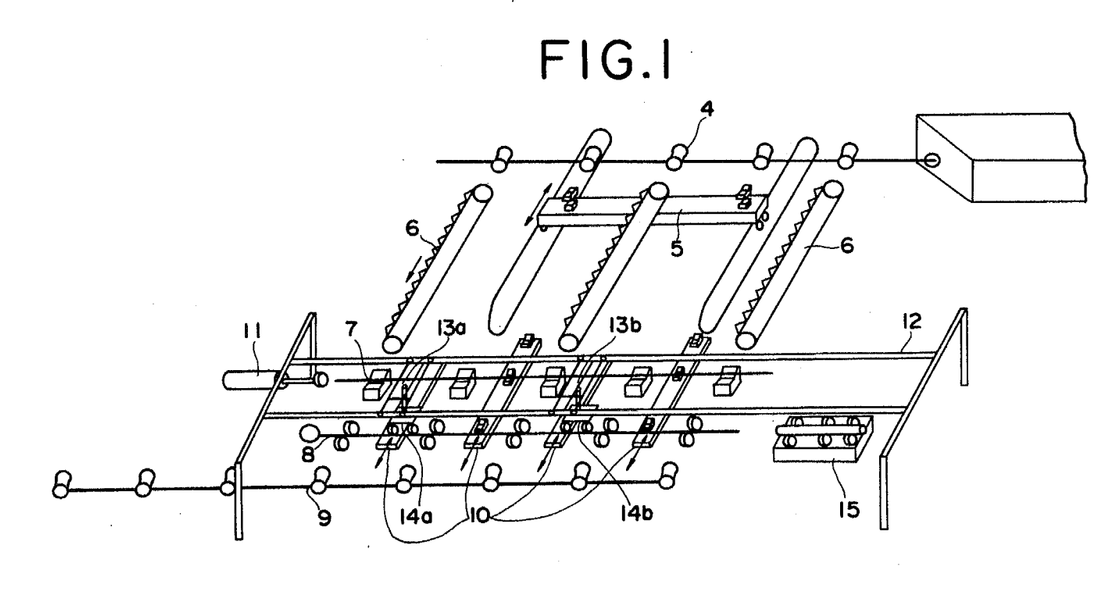
FIG. 1 is a perspective view showing a surface defect detecting apparatus according to an embodiment of the invention.
Figure 2:
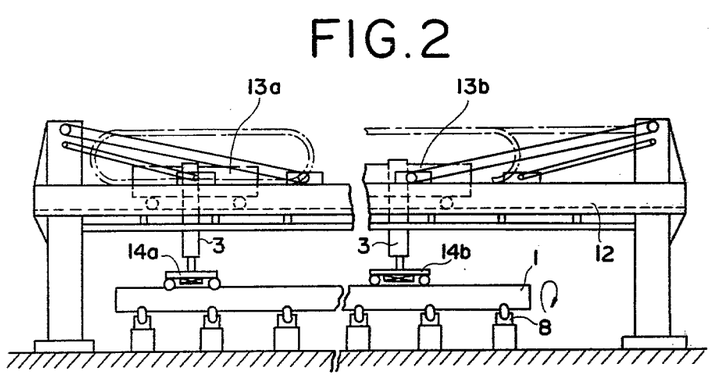
FIG. 2 is a partially cutaway front view of the apparatus shown in FIG. 1.

FIG. 1 is a perspective view showing the overall construction of a surface defect detecting apparatus for round billets according to an embodiment of the invention, and FIG. 2 is a front view showing only the flaw detecting line of the apparatus shown in FIG. 1. In FIGS. 1 and 2, numeral 4 designates the rear table of a preceeding processing equipment or shot blasting equipment and it is connected to a flaw detecting apparatus by way of a rope transfer 5 and a chain transfer 6.

The flaw detecting apparatus includes an end positioning table unit 7 and a turning roller unit 8 which are arranged in parallel to each other, and the apparatus further includes a flaw detection rear table 9 arranged in parallel and connected to the following processing equipment, e.g., a grinding equipment. The apparatus further includes an extractor 10 which is movable in a direction at right angles to the previously mentioned table units, whereby the round billets moved in a transverse direction by the chain transfer 6 are moved, one at a time, onto the end positioning table unit 7 from which the round billet is moved onto the turning roller table unit 8 and further onto the rear table 9. The end positioning table unit 7 includes a hydraulic cylinder-piston unit 11, whereby one end of a billet 1, upon entering the table unit 7, is pushed and located in a predetermined position. Installed above the turning roller table unit 8 is a supporting girder unit 12, and two carriages 13a and 13b are movably hanged on the girder unit 12. Sensor blocks 14a and 14b are respectively suspended from the carriages 13a and 13b so as to be raised and lowered by pressure units or hydraulic cylinder-piston units 3 just above the turning roller table unit 8. Disposed on the extension of the turning roller table unit 8 and within the extent of the girder unit 12 is a calibration turning roller unit 15 which calibrates the sensor characteristics.

With the illustrated embodiment, the carriages 13a and 13b are hanged on the supporting girder unit 12 and their sensor blosks 14a and 14b respectively inspect for defects the halves of the length of the round billet 1 with a small amount of overlapping, thus reducing to half the time required for inspecting the entire length of the billet 1 for defects. In the Figures, the left end of the round billet 1 is located in the predetermined position by the end positioning table unit 7 and simultaneously its length is measured. Then, the extractor 10 moves the billet 1 parallely onto the turning roller table unit 8 where the billet 1 is rotated at a predetermined constant peripheral speed. The supporting girder unit 12 includes a position sensor, e.g., limit switch (not shown) at a position corresponding to the predetermined end position as well as at each of a plurality of middle points, whereby the carriage 13a is stopped at the predetermined left end position detected by the position sensor and the other carriage 13b is stopped at a position which is deviated to the left by an amount corresponding to a predetermined overlap from the central position and detected by one of the position sensor at the plurality of middle points which is selected in accordance with the result of the previous measurement of the length, thus placing the carriages 13a and 13b in condition for initiating flaw detection. In this ready condition, the sensor blocks 14a and 14b which are vertically movably suspended from the carriages 13a and 13b, are pressed into contact with the surface of the round billet 1, and the end of the round billet 1 is inspected for defects by its rotation over one revolution to reduce the uninspected end portion. Thereafter, the outer surface of the round billet 1 is spirally scanned entirely as the carriages 13a and 13b are moved to the right.

Figure 3:
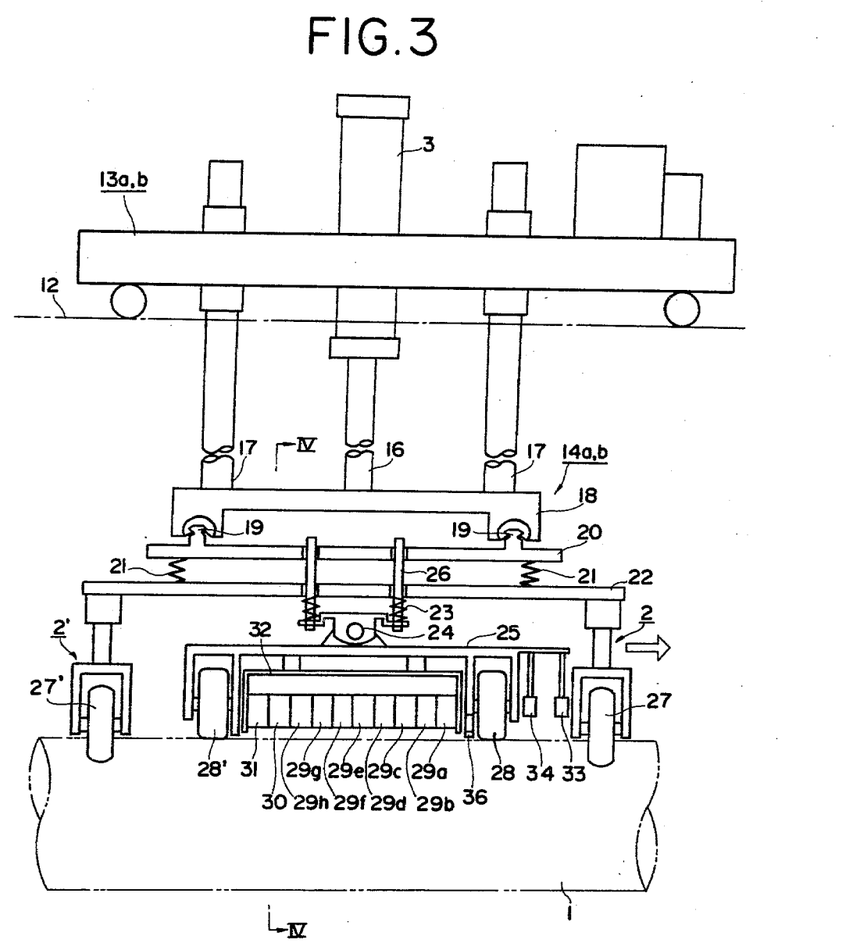
FIG. 3 is an enlarged front view of a sensor block.
Figure 4:
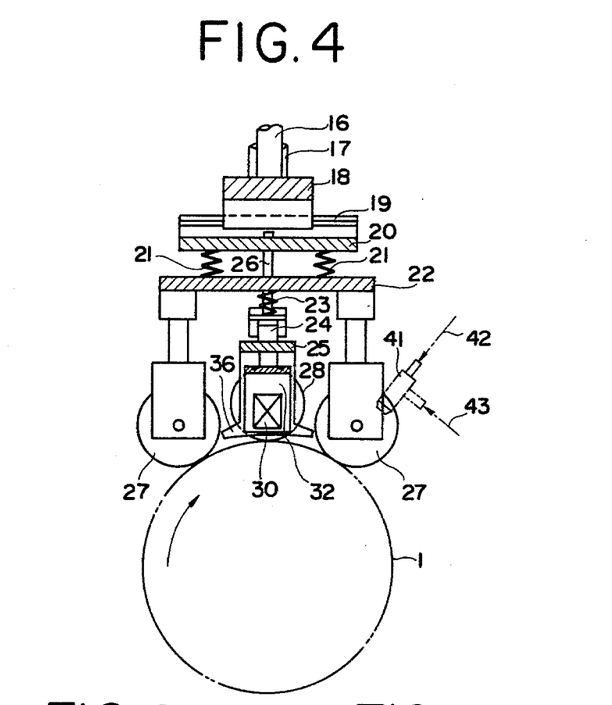
FIG. 4 is a view looked in the direction of the arrow line IV—IV of FIG. 3.

Each of the sensor blocks is constructed as shown in FIGS. 3 and 4, that is, it comprises a base member 18 which is suspended from the carriage by a vertically movable press shaft 16 coupled to the piston rod of a hydraulic cylinder piston unit 3 attached to the carriage and guide shaft 17 for vertically guiding the base member 18 relative to the carriage, and mounted to the base member 18 is a slide base plate 20 which is slidable in a horizontal direction at right angles to the direction of travel of the carriage by means of sliders 19 consisting of slide bearings so as to cause the base member 18 to follow the swing or oscillation of the round billet 1 due to its bend. A follow-up base plate 22 is suspended from the slide base plate 20 by coil springs 21 constituting first pressure or resilient means, and a sensor holder 25 is suspended from the base plate 22 by means of second pressure or resilient means or springs 23 (volute springs) by way of a hinge 24. In other words, the sensor holder 25 is rotatable about the hinge 24 in a vertical plane along the direction of travel of the carriage relative to the base member 18. The sensor holder 25 is also adapted to receive the pressing force applied by the vertically movable press shaft 16 through the springs 21 and 23 so as to be pressed against the round billet 1. Disposed inside the sensor holder 25 are a plurality of eddy-current flaw detection coils 29a, 29b, 29c, 29d, 29e, 29f, 29g, 29h and 30 and a distance detecting coil 31 which are arranged in a row in the direction of travel of the carriage or in the lengthwise direction of the round billet 1 and held in place to face downward, and consequently the lower surface of each coil is opposite to the outer surface of the round billet 1 rotated by the turning rollers with a predetermined gap therebetween. As a result, by virtue of the rotation of the round billet 1 and the movement in the lengthwise direction of the round billet 1 of the sensor block 14a or 14b caused by the carriages, the surface of the round billet 1 will be scanned spirally by the coils 29a to 29h and 30 at a scanning width corresponding to the total widthwise dimension of these coils. Shafts 26 are guide shafts which are secured at their lower ends to the hinge 24 and slidably extended through the base plates 20 and 22.

Mounted respectively to the front and rear parts of the base plate 22 is a pair of follow-up wheel units 2 and 2' respectively comprising follow-up guide wheels 27, 27 and 27', 27' which are respectively arranged on both sides of the direction of movement so as to be spaced away from each other, and in this way each pair of the guide wheels are pressed by the pressing force of the cylinder-piston unit 3 against the sides of the outer surface of the round billet 1 with its top interposed between the wheels as shown in FIG. 4. A pair of turning wheels 28 and 28' are respectively mounted to the front and rear parts of the sensor holder 25 positioned inside the area enclosed by the four guide wheels 27, 27, 27' and 27', and the turning wheels 28 and 28' are pressed by the pressing force of the cylinder-piston unit 3 against the round billet surface to maintain at a predetermined value, e.g., 5 mm the dimension of the gap between the round billet surface and the lower surface of the eddy-current flaw detecting coils 29a to 29h and 30 and the distance detecting coil 31 disposed between the turning wheels 28 and 28'. These coils are fixedly mounted to the sensor holder 25 by means of a holder 32 made of a nonmagnetic material, and proximity switches 33 and 34 are also mounted at a predetermined spacing to the front part of the sensor holder 25 so as to detect the position of the round billet end.

Figure 5:
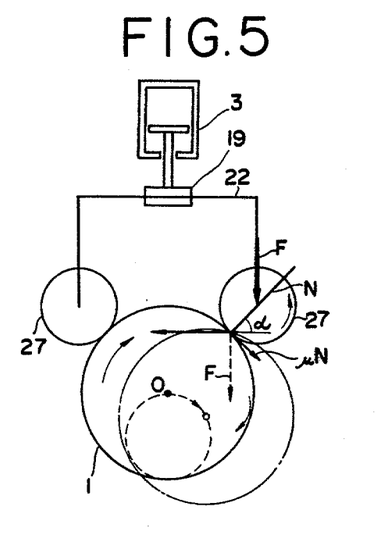
FIG. 5 is a diagram useful for explaining the function of a follow-up wheel unit.

With the sensor block constructed as above described, if the round billet 1 having for example a bend is rotated, it is believed that its center O orbits to describe a path as shown by the dotted line in FIG. 5. If F is the pressing force applied by the hydraulic cylinder-piston unit 3, W is the suspension load of the shaft 16 for the follow-up wheel units, the sensor holder, the supporting base member, the slide base plate, the follow-up base plate, etc., and fc is the opposing force to F which is applied as a reaction force to the cylinder-piston unit 3 when the guide wheels are pressed against the round billet, then we obtain $$F = W - fc \qquad (1)$$

Consequently, the guide wheels 27 provide the desired bilateral follow-up to the bending when the magnitude of the force F, the contact angle $\alpha$. Between the guide wheels 27 and the round billet 1 and the resistance fs for the bilateral movement of the sliders 19 satisfy the following equation (2)

$$F \cot \alpha > fs \qquad (2)$$

However, the rational friction resistance between the guide wheels and the round billet is ignored in the above equation (2). Also with respect to the vertical movement, a satisfactory follow-up will be ensured up to the following acceleration $\dot{V}$ $$\dot{V} < \frac{W - fc}{W} \cdot g \qquad (3)$$

where g is the acceleration by gravity. In other words, in FIG. 5, when the guide wheel contacts with the round billet under the downward force F at the angle $\alpha$, a reaction force N is produced in the guide wheel in the direction of the angle $\alpha$, and a frictional force $\mu N$ is produced in a direction at right angles to the reaction force N. Thus, an inwardly acting follow-up force $F \cot \alpha$ is produced which is balanced with the former forces. As a result, if $F \cot \alpha > fs$, assuming $\mu << 1$, $F = N \sin \alpha - \mu N \cos \alpha$ becomes $F = N \sin \alpha$ and the base plate 22 makes the bilateral follow-up motion at an acceleration which is determined by $F \cot \alpha - fs$.

To determine the above-mentioned conditions, the diameter and spacing of the guide wheels 27, the stroke of the cylinder-piston unit 3, the stroke of the sliders 19, etc., are determined in consideration of the outer diameter, magnitude of bend and rotational speed of the material to be inspected, the weight of the sensor block itself, various frictions, etc., and by adjusting the pressing force applied by the cylinder-piston unit 3 the same follow-up means ensures the desired follow-up movement to materials to be inspected having outer diameters falling within certain limits. In this case, to ensure a longer life and stable operation over a long period of time for the guide wheels which contact the material, the bearings used, etc., the cylinder-piston unit 3 may be adapted to produce a negative pressure to reduce the contact pressure between the guide wheels and the material to the minimum limit required for providing the follow-up action. For example, where the sensor block is supported in a suspended manner so that the total weight of the sensor block itself is applied to the contact points between the round billet and the guide wheels and this total weight is greater than that required for the purpose of follow-up action, the cylinder-piston unit 3 produces an upward force which acts to lift the sensor block. As regards the magnitude of this force fc', the desired contact between the material and the guide wheels will be ensured if the following equation (4) is satisfied by the piston frictional force fp of the cylinder-piston unit 3, the maximum amplitude of bend A of the material and the rotational speed n (rpm) of the material $$A \left( \frac{2\pi n}{60} \right)^2 < \frac{W - fc' - fp}{W/g} \qquad (4)$$

While the external sectional form of materials is not always a perfect round form and they may be of various irregular shapes as will be mentioned later thus placing a limit to the magnitude of the force fc', by controlling the pressure in accordance with the above equation (4) it is possible to greatly reduce the wear of the component parts, e.g., the guide wheels, bearings, etc., caused by the contact pressure.

Figure 6A:
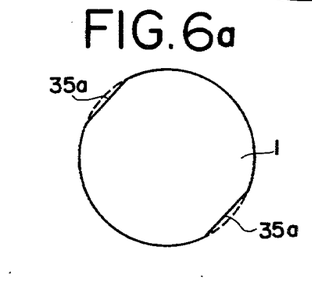
FIGS. 6a and 6b are end views showing round billet ovals.
Figure 6B:
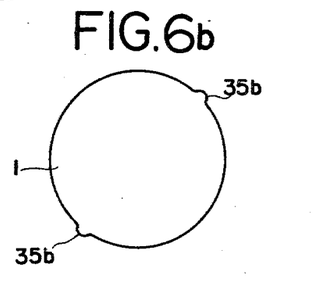

As shown in FIGS. 6a and 6b, the round billet 1 usually includes concave ovals 35a or convex ovals 35b, so that when the oval approaches the lower parts of the coils by the rotation of the round billet 1, due to the fact that in the above-described sensor block the holder 25 is supported by way of the springs 23 and the turning wheels 28 and 28' follow up the oval thus maintaining the gap just below the coils at a predetermined value, there is no danger of the coils being damaged by the oval projections and the value of the gap between the coils and the billet outer surface is always maintained constant with the resulting preventing of any change in the detection characteristic.

Also provided at the end of the holder 25 on the side of the billet end, is a protector 36 which projects beyond the lower surface of the coils and positioned above the lower end of the turning wheel so as to protect the coils from being damaged by the edge of the billet end in the event that the turning wheel 28 falls off.

Figure 7:
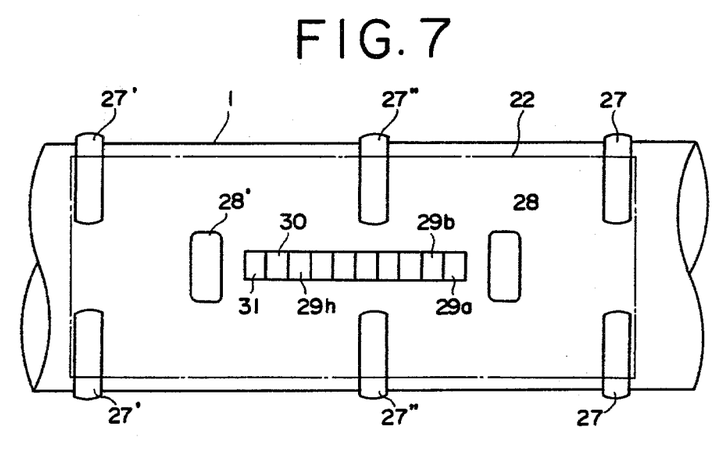
FIG. 7 is a plan view showing another form of arrangement of the guide wheels.

The first and second proximity switches 33 and 34 are provided to detect the round billet end prior to the coils, and the sequence is determined in such a manner that the carriage travel speed is decreased in response to the detection of the billet end by the first proximity switch 33, the travel speed is further decreased, and then when the billet end is detected by the second proximity switch 34, after a predetermined time delay the movement of the carriage is stopped in such a manner that the turning wheel 28 is located on the billet end as far as possible. On the other hand, in order that the gap between the lower surface of the coils and the round billet surface may be maintained constant and the surface flaw detection may be effected by following the bend even in the event of the leading guide wheels falling off the round billet end, as shown in FIG. 7, one or both of another guide wheels 27", 27" which are similar to the guide wheels 27 and 27', may be mounted to the follow-up base plate 22 to position at least on one side or on both sides of the sensor holder. In this case, even the leading guide wheels 27, 27 fall off the round billet end, the desired follow-up action is provided by the guide wheels 27", 27" and 27', 27' to conform with the bend so that the desired flaw detection is effected until the leading turning wheel 28 moves past the round billet end and consequently the uninspected end portion is reduced to a very small portion corresponding to the dimension of the spacing between the turning wheel 28 and the first coil 29a.

Figure 8:
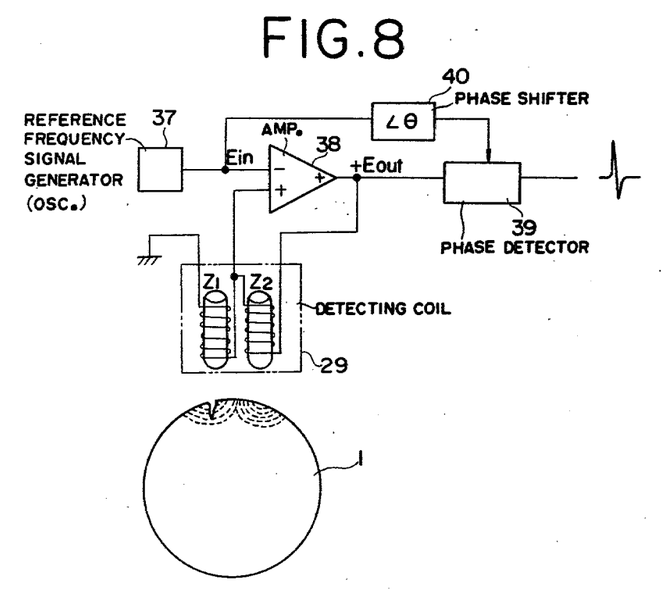
FIG. 8 is a circuit diagram of a basic flaw detecting circuit.

FIG. 8 shows the basic construction of a flaw detecting circuit in which a reference frequency signal generator 37 applies an AC signal to the eddy-current flaw detecting coil 29 through an amplifier 38 to produce eddy currents in the round billet 1, whereby a change in the eddy currents associated with a defect is detected as a change in the coil impedance and a flaw detection output signal is generated from a phase detector 39. In the Figure, numeral 40 designates a phase shifter for generating a synchronizing signal for phase detection purposes. In this case, if Ein represents the input voltage or reference signal to the amplifier 38 and $Z_1$ and $Z_2$ represent the impedances of the two coil elements constituting the flaw detecting coil, the resulting output signal Eout is given by $$E_{out} = E_{in} \cdot \frac{G}{1 - G \cdot \frac{Z_1}{Z_1 + Z_2}}$$

where G is the gain of the amplifier 38. By suitably selecting the value of the coil impedances $Z_1$ and $Z_2$ under the standard condition, it is possible to change the feedback ratio of the circuit, and also by changing the amplification degree of the amplifier 38 and the flaw detecting phase, it is possible to change the range in which an output having a good linearity with respect to the depth of defects can be produced. As a result, by selecting the flaw detecting coils 29a to 29h as small and medium flaw coils which show the desired linearity for all defects which are 5 mm deep or smaller and selecting the flaw detecting coil 30 as a large flaw coil which shows the desired linearity for defects over 5 mm deep, it is possible to discriminate the defects in a plurality of ranges. Further, since the coil shape changes this characteristic, the large flaw coil alone may be increase in size.

With the circuit of FIG. 8, the distance detecting coil 31 is connected to a distance detecting circuit which performs linear detection instead of phase detection and its output is used as a control signal for an automatic gain control amplifier circuit (the AGC circuit) following the detector output in FIG. 8.

With the embodiment shown in FIG. 3, if the coils 29a to 29h each has a width of 18 mm or a total width of 144 mm and if the flaw detecting pitch is selected 135 mm, that is, the flaw detecting lapping percentage (144−135)/144=0.06(6%) and the peripheral speed $V_r$ for rotating the round billet by the turning rollers is held constant at 500 mm/sec, the carriage travel speed V is determined by the outer diameter d(mm) of the round billet as given by the following equation $$V = \frac{135 \cdot V_r}{\pi d} = \frac{21496.8}{d}$$

Although not shown, the carriage drive unit includes a control unit whereby the carriage travel speed is controlled automatically by setting the diameter of the billet entered in accordance with the above equation.

As shown in FIG. 4, each of the sensor blocks 14a and 14b is provided with marking paint spray nozzles 41 which are for example supported by the holder 25 in such a manner that each nozzle is directed to the round billet surface delayed a predetermined distance from just below the coil with respect to the direction of rotation of the round billet. This predetermined distance is determined in accordance with the peripheral speed of the billet rotated by the turning rollers, and it is so designed that the location detected by the coil arrives just below the nozzle after a certain delay time in the signal system and the working system. For example, it may be arranged so that when a defect is detected by any of the small and medium flaw coils 29a to 29h, white paint is sprayed from the nozzle mounted in the position corresponding to the coil, and when a defect is detected by the large flaw coil 30, red paint is sprayed from another nozzle mounted in the position corresponding to the coil 30. In FIG. 4, a pipe line 42 connected to the nozzle 41 is a paint line, and a pipe line 43 is a compressed air line. Although not shown, a paint tank and a pump are connected to the paint line 42 through a solenoid valve which is not shown, and a compressed air source is connected to the air line 43, thus allowing the air line 43 to serve an additional function of always blowing air and removing the dust and the like on the outer surface of round billets. The solenoid valve is actuated by a flaw signal detected by the coil so that paint is supplied to the nozzle and the paint is sprayed from the nozzle at the instant that the detected defect arrives just below the nozzle.

Figure 9:
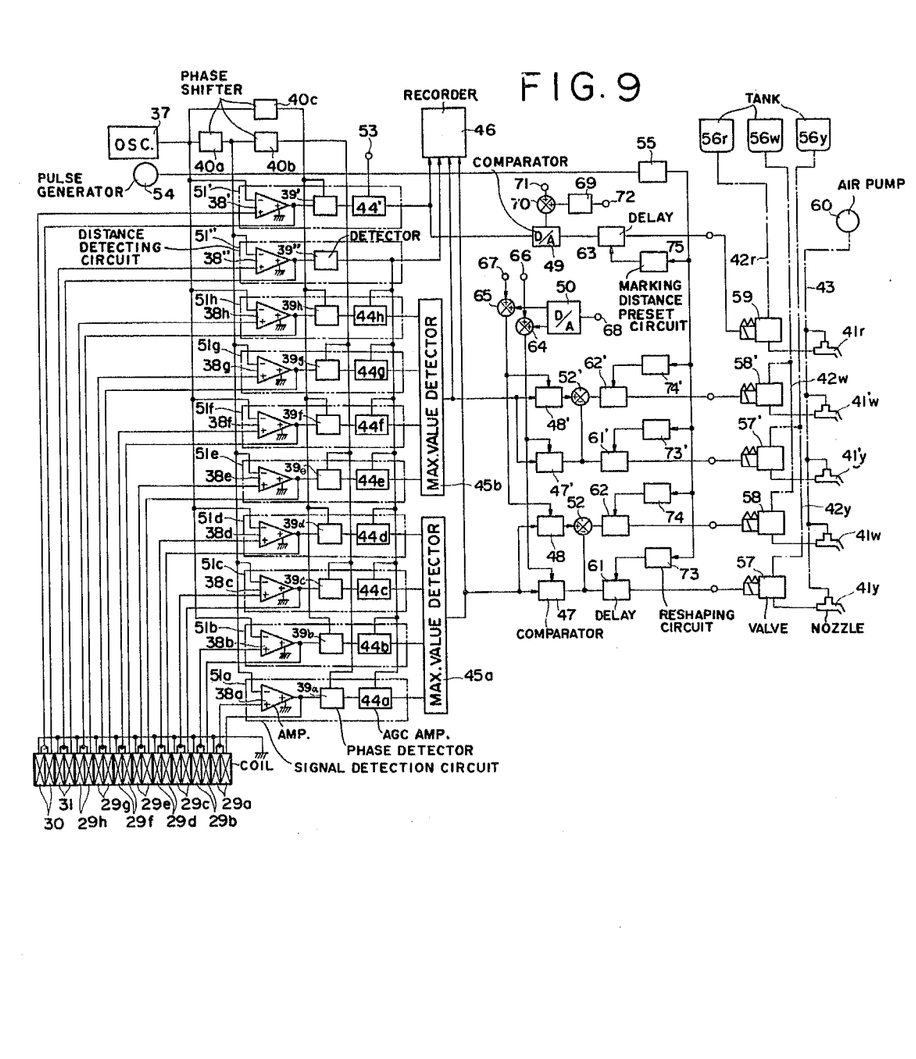
FIG. 9 is a block diagram showing a flaw detecting system used with the embodiment of the invention.

FIG. 9 shows the construction of a more elaborate flaw detecting circuit. FIG. 9 is a block diagram of a flaw detecting system for use with the present invention in detecting defects in the surface of round billets, and each sensor used comprises ten coils closely arranged in a row. In the Figure, coils 29a to 29h and 30 are flaw detecting coils for surface defect detecting purposes, and a coil 31 is a distance detecting coil. The coils 29a to 29h are respectively connected to flaw signal detection circuits 51a to 51h, the coil 31 is connected to a distance detecting circuit 51″, and the coil 30 is connected to another flaw signal detection circuit 51′.

The flaw signal detection circuits 51a to 51h and 51′ respectively comprise feedback amplifiers 38a to 38b and 38′ each including a positive feedback loop provided by the two coil elements of the associated coil as mentioned previously, phase detectors 39a to 39h and 39′ for respectively subjecting the output of the associated amplifier to phase detection and automatic gain control amplifiers 44a to 44h and 44′, and the detection output of each phase detector is subjected to gain adjustment by the automatic gain control amplifier to generate a flaw detection output.

The distance detecting circuit 51″ comprises a feedback amplifier 38″ similarly including a positive feedback loop provided by the two coil elements of the distance detecting coil 31 and a detector 39″ for subjecting the output of the amplifier 38″ to linear detection, and the output of the detector 39″ is applied as a gain control signal to the automatic gain control amplifier 44a to 44h of the flaw signal detection circuits 51a to 51h. In the illustrated embodiment, the automatic gain control amplifier 44′ of the separate flaw signal detection circuit 51′ alone receives a separate gain control signal consisting of a preset signal applied to a preset input terminal 53.

As mentioned previously, each of the coils forms a separate signal system and the coils are formed into two signal system groups one including the coils 29a, 29c, 29e, 29g and 31 and the other group including the coils 29b, 29d, 29f, 29h and 30. More specifically, in one signal system group the respective coils are energized by the AC signal generated from the oscillator 37 for generating reference frequency AC signal, shifted in phase by α° through a first phase shifter 40a and then applied to the amplifiers 38a, 38c, 38e, 38g and 38″, respectively, and in the other signal system group the respectively coils are energized by the AC signal applied directly from the oscillator 37 to the amplifiers 38b, 38d, 38f, 38h and 38'. Thus, in each sensor every other coil is energized by an AC signal which is different in phase by $\alpha°$ from that applied to the adjoining coil. Each of the energized coils causes eddy currents in the round billet surface just below the coil and consequently a change in the eddy currents associated with a defect or a change in the dimension of the gap is detected as a change in the coil impedance. The output signal of the amplifiers 38a to 38h and 38', respectively, is subjected to phase detection by the phase detectors 39a to 38h and 39', respectively. More specifically, in one signal circuit group the phase detectors 39a, 39c, 39e and 39g each receives as a synchronizing signal the output of the oscillator 37 which was shifted in phase by the phase shifter 40a and further shifted by $\beta$ degrees by a second phase shifter 40b to have the optimum flaw detecting phase, and in the other signal circuit group the phase detectors 39b, 39d, 39f, 39h and 39' each receives as a synchronizing signal the output of the oscillator 37 which was shifted in phase by $\beta$ degrees through another second phase shifter 40c.

Figure 10:
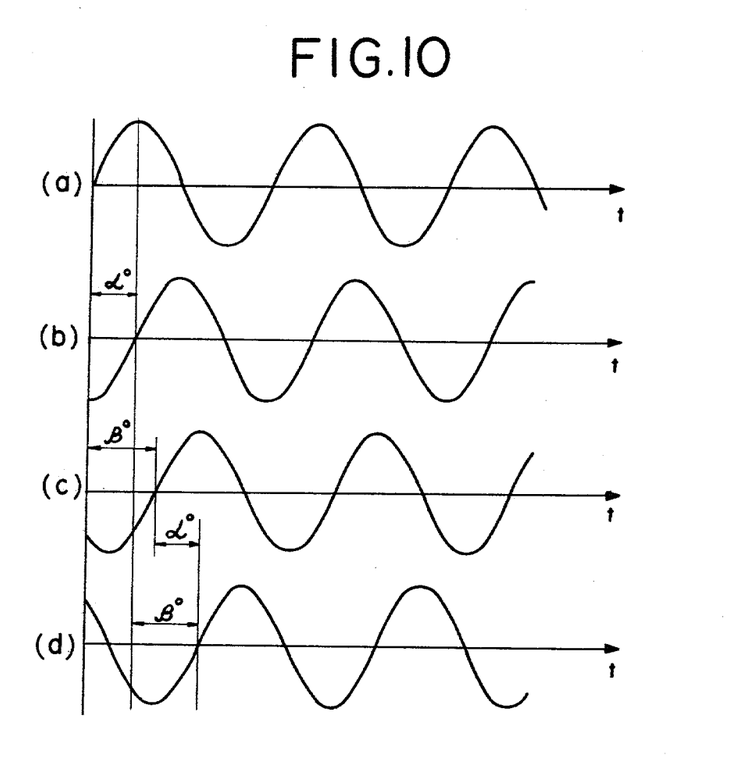
FIG. 10 is a waveform diagram showing the waveforms generated at various points in the system of FIG. 9.

FIG. 10 shows the phase relationships among these signals, namely, the waveform (a) is the output signal of the oscillator 37, the waveform (b) the output signal of the phase shifter 40a, the waveform (c) the output signal of the phase shifter 40c and the waveform (d) the output signal of the phase shifter 40b.

In other words, the synchronizing signal applied to the phase detectors in one of the two signal system groups is different in phase by $\alpha$ degrees from that applied to the phase detectors in the other signal system group, and the energizing signal of each coil is different in phase by $\beta$ degrees from the synchronizing signal applied to the associated phase detector.

In this way, by shifting the phase of the signals applied to the adjoining phase detectors in accordance with the phase difference with respect to the adjoining coils, it is possible to effectively prevent interference between the adjoining coils.

While, in the embodiment described above, the signal processing is accomplished by applying to the two signal system groups the AC signal of the same frequency but different in phase from each other, it is possible to prevent interference between the coils by for example connecting an oscillator to each of the two signal circuit groups, the oscillation frequencies of the oscillators being different from each other by such amount that the flaw detecting characteristic is changed in no way, connecting before each phase detector of one signal system group a high-pass filter having a cutoff frequency intermediate of the oscillation frequencies and connecting before each phase detector of the other signal system group a low-pass filter having the similar cutoff frequency, thus preventing interference by utilizing frequency differences. In any way, only difference is that the phase differences between the two signal system groups are fixed or changed periodically.

In FIG. 9, by suitably selecting the feedback ratio and amplification degree of the amplifiers 38a to 38h and 38' and the flaw detecting phase ($\beta°$), the flaw detecting coils 29a to 29h are selected as small and medium flaw coils which show the desired linearity for all defects 5 mm deep or smaller and the flaw detecting coil 31 is selected as a large flaw coil which shows the desired linearity for defects greater than 5 mm deep so as to discriminate between medium and small flaws and large flaws. In this connection, since the coil shape changes this characteristic, the large flaw coil alone may be increased in size.

In the Figure, numerals 41y and 41'y designate marking nozzles for spraying medium flaw marking yellow paint, 41w and 41'w marking nozzles for spraying small flaw marking white paint, and 41r a marking nozzle for spraying large flaw marking red paint. The nozzles 41y and 41w are mounted to the sensor block so as to be adjacent to each other and placed in positions corresponding to coils 29a, 29b and 29c, 29d, respectively, as in the case shown in FIG. 4, and in the like manner the nozzles 41'y and 41'w are mounted to the sensor block in positions corresponding to the coils 29e, 29f and 29g, 29h, respectively. Also the nozzle 41r is mounted to the sensor block in a position corresponding to the coil 31.

In the Figure, numeral 54 designates a pulse generator for measuring the peripheral speed of the round billet, and its output pulses have a period corresponding to the peripheral speed of the round billet.

Each nozzle sprays the paint at the instant that the defective area detected by the associated coil arrives just below the nozzle after a delay time in the signal system and the working system.

As regards the outputs of the respective flaw signal detection circuits, the outputs of the detection circuits 51a to 51d are applied to a maximum value detector circuit 45a (analog OR circuit) and the outputs of the detection circuits 51e to 51h are applied to another similar maximum value detector circuit 45b, thus providing two channels for the two groups each including the four small and medium flaw coils. The maximum value detectors 45a and 45b each generates an output which is the flaw signal having the highest amplitude among the input signals, and their outputs are respectively branched and applied to medium flaw comparator circuits 47 and 47' and to small flaw comparator circuits 48 and 48'. The comparator circuits compare the amplitude of flaw signal inputs with a reference medium level or small level through adders 64 and 65 in accordance with preset signals by a digital preset input 68 through a D-A converter 50 and a medium flaw comparison level input 66 and a small flaw comparison level input 67, whereby when there is for example an input corresponding to a defect smaller than 2 mm deep, an output is generated from the small flaw comparator circuit 48 or 48', and when there is an input corresponding to a defect greater than 2 mm but smaller than 5 mm deep, an output is generated from the medium flaw comparator circuit 47 or 47 and simaltaneously an output is generated from an adder 52 or 52' to cancel the output of the small flaw comparator circuit 48 or 48'. In the Figure, numeral 46 designates a recorder for recording the flaw detection outputs from the two channels and the large flaw signal detection circuit 51' and the gap signal output of the distance detecting circuit 51".

Also in the Figure, the flaw signal from the large flaw signal detection circuit 51' is applied to the similar large flaw comparator circuit 49 and consequently the amplitude of the large flaw signal is compared through an adder 70 in accordance with a preset signal applied by a digital preset input 72 through a D-A converter 69 and a large flaw comparison level input 71 so as to discriminate defects greater than 5 mm deep, for example. Numerals 61, 62, 61', 62' and 63 designate signal delay circuits, whereby the delay circuits 61 and 61' receive the medium flaw outputs from the channels, the delay circuits 62 and 62' receive the small flaw outputs from the channels, and the delay circuit 63 receives the large flaw output. The peripheral speed pulses from the pulse generator 54 are applied to the delay circuits through a reshaping circuit 55 and marking distance preset circuits 73, 74, 73', 74' and 75. Solenoid valves 57, 58, 57', 58' and 59 are each connected to the output of associated one of the delay circuits, and consequently each delay circuit applies an energizing signal to the solenoid of the associated solenoid valve after a predetermined delay time preset in the delay circuit from the time of application of the flaw output thereto. In other words, the supply of paint from pressure paint tanks 56y, 56w and 56r to the nozzles 41y, 41w, 41'y, 41'w and 41r is controlled by the solenoid valves so that when the flaw signal is applied to the delay circuit, the paint is sprayed after a delay time including a delay time in the operation of the paint supply system and determined in accordance with the round billet peripheral speed measured by the pulse generator 54 and the nozzle-to-coil distance. In the Figure, the nozzles 41y and 41'y are respectively controlled by the solenoid valves 57 and 57' connected to the tank 56y through a pipe line 42y, and consequently the nozzles 41y and 41'y are respectively responsive to the medium flaw outputs from the two channels to respectively spray the yellow marking paint just below the coils 29a, 29b and 29e, 29f, respectively. On the other hand, the nozzles 41w and 41'w are respectively controlled by the solenoid valves 58 and 58' connected to the tank 56w through a pipe line 42w, and consequently the nozzles 41w and 41'w respectively spray the white marking paint just below the coils 29c, 29d and 29g, 29h in response to the small flaw outputs of the two channels. The nozzle 41r is also controlled by the solenoid valve 59 connected to the tank 56r through a pipe line 42r, and consequently the nozzle 41r sprays the red marking paint just below the coil 31 in response to the large flaw output. In the Figure, numeral 60 designates a compressed air source for the nozzles, and 43 an air pipe line, whereby the compressed air is always supplied to the respective nozzles even when there is no supply of paint thereto, and consequently the nozzles always blow air to prevent clogging of the nozzles.

We claim:

1. In a surface defect detecting apparatus having at least one sensor block adapted to be moved in a lengthwise direction of a rotating cylindrically shaped electrically conductive metallic material to be inspected, said material being rotated at a predetermined peripheral speed whereby said detecting apparatus spirally scans an outer portion of the surface of said material, said sensor block being supported by a carriage movable in the lengthwise direction of said material, said sensor block including a pair of guide wheels at each of the front and rear parts thereof disposed in the direction of movement, said pair of guide wheels being directed in said spiral scanning direction in a spaced relation and rotate in response to the rotation of said material in contact with the outer surface thereof, said sensor block further including a coil holder supporting a plurality of eddy-current flaw detecting coils arranged in a row longitudinal to the direction of movement, intermediate between said pairs of guide wheels at said front and rear parts so as to be opposite to the outer surface of said material with a predetermined gap therebetween, said coil holder including a turning wheel at each of the front and rear parts thereof in the direction of said movement, each of said turning wheels being directed in said spiral scanning direction and rotatable in contact with the outer surface of said material so as to maintain said predetermined gap, the improvement comprising: means whereby an AC signal of a predetermined frequency is applied from an osciallator to said plurality of flaw detecting coils arranged in a row, to cause each of said coils to produce corresponding eddy currents in said material to be inspected disposed opposite to said coils; said coils are divided into at least a first group and a second group, said first group of coils being defined by coils alternating with the coils of said second group in said row, the oscillator providing the AC signal to said first group of coils and to phase shifter means, said phase shifter means providing a first phase shifted AC signal shifted in phase by a predetermined amount for delivery to a first plurality of phase detectors associated with said first group of coils, said phase shifter means further providing a second phase shifted AC signal to said second group of coils, shifted in phase a predetermined amount from the phase of the AC signal provided to the first group of coils and different in phase from the phase of the first phase shifted AC signal, said phase shifter means further providing a third phase shifted AC signal to a second plurality of phase detectors associated with said second group of coils, the third phase shifted AC signal being shifted in phase a predetermined amount from the second phase shifted AC signal and different in phase from the first phase shifted AC signal and the AC signal provided to the first group of coils.

2. A surface defect detecting apparatus according to claim 1, wherein said sensor block is adapted to sit on material to be inspected having a circular external shape, for example, a round bar, and rotatable about a lengthwise axis, and wherein said sensor block comprises a supporting base member movable in an upward and downward direction from a carriage disposed on a supporting girder means, said carriage being movable in an axial direction of the cylindrical metallic material; a slide base plate mounted to said supporting base member slidable in a direction at right angles to the lengthwise direction of said material, a pair of follow-up wheel units each thereof including a pair of said guide wheels directed in said sliding direction in a spaced relation and in contact with the outer surface of said material so as to be turned by the rotation thereof, a follow-up base plate supporting said pair of follow-up wheel units in a spaced relation in the lengthwise direction of said material and coupled to said slide base plate through first resilient means in a direction to press said follow-up wheel units against said material, said coil holder coupled within the space between said pair of follow-up wheel units to said follow-up base plate in said pressing direction through second resilient means so as to be rotatable about an axis directed in said sliding direction, a turning wheel mounted to each lengthwise end of said holder within the space between said follow-up wheel units and adapted to be turned by the rotation of said material in contact with the surface thereof so as to maintain at a predetermined value the dimension of the gap between a lower surface of said coils mounted to a central portion of said holder and the surface of said material, and pressure means mounted to said carriage to press said supporting base member so as to press said guide wheels and said turning wheels against the surface of said material through said slide base plate, said follow-up base plate and said first and second resilient means.

3. A surface defect detecting apparatus according to claim 2, wherein another turning wheel is supported on said follow-up base plate at least on one side of the central portion of said holder so as to be turned in contact with the surface of said material.

4. A surface defect detecting apparatus according to claim 2, wherein sensor lower surface protecting means is mounted at least to one end of said holder between said row of the coils and said turning wheel, said protecting means projecting beyond said coil lower surface and having a bottom surface positioned above the lower end of said turning wheel.

5. An apparatus as claimed in claim 1, wherein: the AC signal as fed to the first group of coils and phase detectors of the first group is shifted in phase by 180° with respect to the AC signal respectively fed to the second group of coils and phase detectors of said second group.

* * * * *